(12) United States Patent
Vaes

(10) Patent No.: US 8,759,011 B2
(45) Date of Patent: Jun. 24, 2014

(54) ASSAY SYSTEM FOR DETERMINING BINDING OF HYDROPHOBIC DRUGS

(75) Inventor: Wouter Henricus Johannes Vaes, Utrecht (NL)

(73) Assignee: Nederlandse Organisatie voor toegepast-natuurwetenschappelijk onderzoek TNO (NL)

( * ) Notice: Subject to any disclaimer, the term of this patent is extended or adjusted under 35 U.S.C. 154(b) by 97 days.

(21) Appl. No.: 13/263,657

(22) PCT Filed: Apr. 8, 2010

(86) PCT No.: PCT/NL2010/050189
§ 371 (c)(1),
(2), (4) Date: Dec. 27, 2011

(87) PCT Pub. No.: WO2010/117276
PCT Pub. Date: Oct. 14, 2010

(65) Prior Publication Data
US 2012/0100634 A1    Apr. 26, 2012

(30) Foreign Application Priority Data
Apr. 9, 2009   (EP) ..................................... 09157791

(51) Int. Cl.
*G01N 33/53* (2006.01)
(52) U.S. Cl.
USPC ............................................. 435/7.1; 435/7.2
(58) Field of Classification Search
None
See application file for complete search history.

(56) References Cited

U.S. PATENT DOCUMENTS

| 4,888,275 | A | * | 12/1989 | Holmgren et al. | ............ | 435/7.23 |
| 5,175,148 | A | * | 12/1992 | O'Rand et al. | ............. | 424/185.1 |
| 6,310,247 | B1 | * | 10/2001 | Cheung et al. | ................ | 564/180 |
| 2009/0026122 | A1 | | 1/2009 | Pawliszyn et al. | | |
| 2009/0048439 | A1 | * | 2/2009 | Weisburg et al. | .......... | 536/25.41 |

OTHER PUBLICATIONS

Abdel-Rehim M. et al., "Evaluation of solid-phase microextraction for the study of protein binding in human plasma samples," Journal of Chromatographic Science, Preston Publications, Niles, IL US, vol. 38, No. 10 (Oct. 1, 2000), p. 458-464, XP009120862.
Musteata, Florin Marcel et al., "Study of ligand-receptor binding using SPME: Investigation of receptor, free, and total ligand concentrations," Journal of Preoteome Research, vol. 4, No. 3 (May 2005), pp. 789-800, XP 002542329.
International Search Report for PCT/NL2010/050189, 2010.

* cited by examiner

*Primary Examiner* — Jacob Cheu
(74) *Attorney, Agent, or Firm* — Banner & Witcoff, Ltd.

(57) ABSTRACT

The invention comprises a method for the determination of the binding coefficient of a hydrophobic chemical compound comprising: g. Providing an assay plate with a plurality of rows and columns of test vessels; h. Providing the majority of the test vessels in said assay plate with a polymer, wherein in each row the amount of polymer coating per test vessel is increased; i. Filling each test vessel with a solution of binding partner to which the binding coefficient should be assayed, wherein in each column the amount of binding partner is increased; j. Adding the hydrophobic compound and incubate the plate; k. Determining the concentration of said compound in said polymer or in the solution; l. Calculating the protein binding coefficient of the compound.

14 Claims, 2 Drawing Sheets

ASSAY SYSTEM FOR DETERMINING BINDING OF HYDROPHOBIC DRUGS

CROSS-REFERENCE TO RELATED APPLICATIONS

Figure 1:
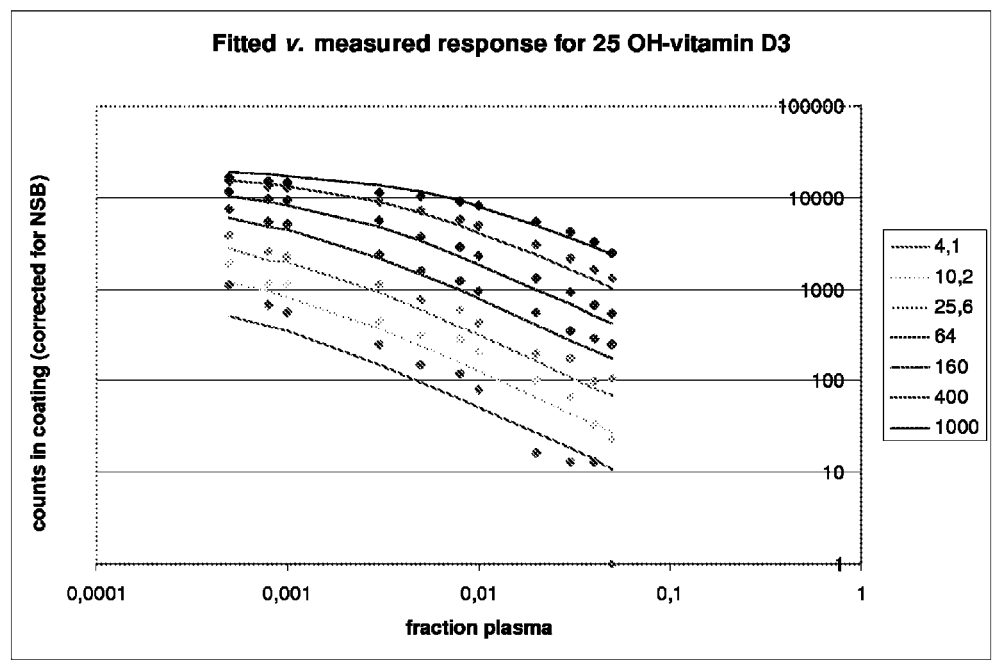

This application is a U.S. National Stage application under 35 U.S.C. §371 of International Application PCT/NL2010/050189 (published as WO 2010/117276 A1), filed Apr. 8, 2010, which claims priority to Application EP 09157791.6, filed Apr. 9, 2009. Benefit of the filing date of each of these prior applications is hereby claimed. Each of these prior applications is hereby incorporated by reference in its entirety.

FIELD OF THE INVENTION

The invention relates to the field of determining the bioactivity of molecules, especially assaying for binding of hydrophobic compounds, more specifically protein binding of hydrophobic compounds.

BACKGROUND ART

In the development of new drugs, one of the important characteristics is the binding of the new chemical entity (NCE) to receptors or other cellular proteins, while binding to plasma proteins or to untargeted cellular components, such as lipid membranes often is an unwanted side-effect and could be detrimental for the pharmaceutical activity.

A drug's efficiency may be affected by the degree to which it binds to untargeted cellular components or to the proteins within blood plasma. The less bound a drug is, the more efficiently it can traverse cell membranes or diffuse. Protein binding can influence the drug's biological half-life in the body. The bound portion may act as a reservoir or depot from which the drug is slowly released as the unbound form. Since the unbound form is being metabolized and/or excreted from the body, the bound fraction will be released in order to maintain equilibrium.

Thus, knowledge about the amount of plasma protein or cellular component binding is essential to predict the behaviour of the drug in the body and to establish a rationale on dose-effect relationships.

Nowadays, measuring binding to plasma proteins is accomplished by an equilibrium dialysis, from which affinity/binding coefficients can be measured (see e.g. Shibukawa, A. et al., 1994, J. Pharm. Sci. 83:868-873; Minagawa, T. et al., 1994, J. Pharm. Pharmacol. 46:838-843; Curry, S. H. et al., in: Analysis of Psychotropic Drugs, Ed: Boulton, A. A. et al., Springer Protocols: Neuromethods, Vol. 10, p. 1-31). However, some NCEs, notably hydrophobic NCEs, have such fysico-chemical properties, which makes them incompatible with the current technologies, that equilibrium dialysis is no longer feasible. The above-mentioned prior art all mention special techniques for equilibrium dialysis techniques to be able to measure the interaction between hydrophobic drugs and plasma proteins.

Thus, there is still need for a simple and reliable method to assay the affinity/binding coefficients of hydrophobic small chemical compounds to proteins or biological, i.e. cellular components.

SUMMARY OF THE INVENTION

The inventors now have found a method to determine the protein binding coefficients of hydrophobic compounds in a simple and reliable manner.

The invention comprises a method for the determination of the binding coefficient of a hydrophobic chemical compound comprising:
a. Providing an assay plate with a plurality of rows and columns of test vessels;
b. Providing the majority of the test vessels in said assay plate with a polymer, wherein in each row the amount of polymer coating per test vessel is increased;
c. Filling each test vessel with a solution of binding partner to which the binding coefficient should be assayed, wherein in each column the amount of binding partner is increased;
d. Adding the hydrophobic compound and incubate the plate;
e. Determining the concentration of said compound in said polymer or in the solution;
f. Calculating the protein binding coefficient of the compound.

Preferably, in said method the assay plate is a 96-wells microtiter plate. In a further preferred embodiment, the polymer is a thin film polymer, and preferably said polymer is coated in each well. Specifically preferred is a method according to the invention wherein the polymer is a lipophilic polymer, preferably selected from the group consisting of polysiloxanes polyacrylates, divinylbenzene, carboxylated PVC, cellulose acetate, "molecular imprinted polymers" (MIPs), and mixtures thereof, more preferably dimethylsiloxane. Further preferred is a method according to the invention, wherein said binding partner is a protein, preferably a plasma protein, more preferably selected form the group consisting of human serum albumin, immunoglobulins and lipoproteins, preferably wherein said binding partner is a cellular component, preferably a lipid vesicle or a lipid membrane.

Further preferred is a method according the invention, wherein the protein solution is an aqueous solution, preferably plasma.

LEGENDS TO THE FIGURES

FIG. 1: Graph showing datapoints and curves fitted thereto for an assay according to the invention with 25-OH vitamin D3. The X-axis denotes the fraction of human plasma in the total solution (in ml/ml), while the Y-axis relates to the counts for each specific volume of polymer coating (in nl, given for each curve) in each well. As expected, increasing the fraction of human plasma leads to lower partitioning to the polymer coating, and increasing the polymer coating leads to a higher partitioning to the coating. Experiments were conducted in 96 well plates, where the total volume was 200 µl.

Figure 2:
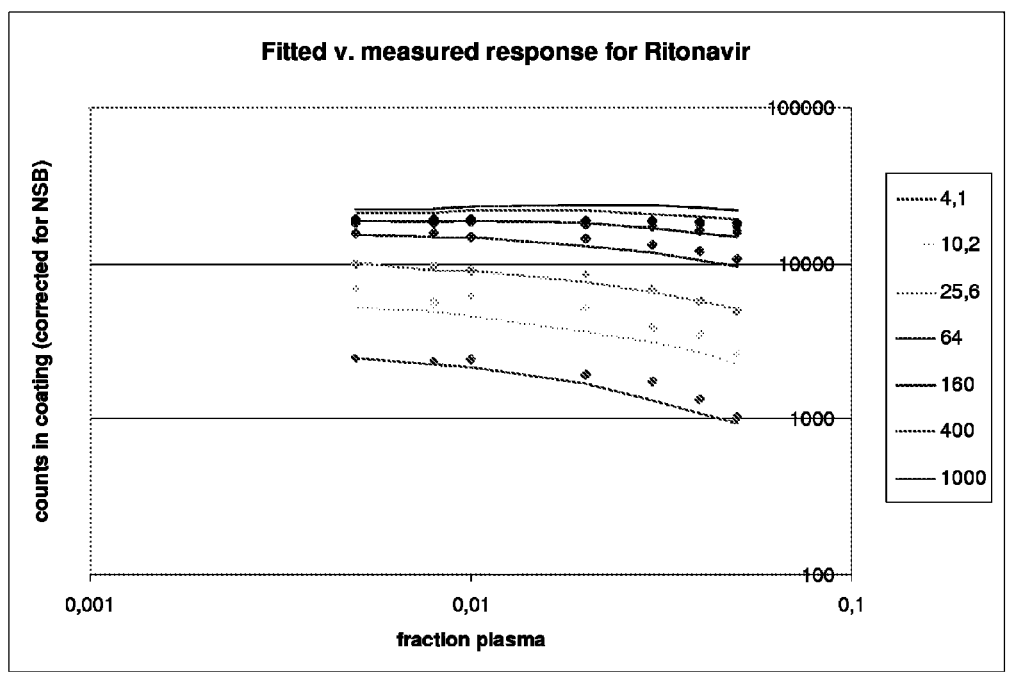

FIG. 2: Graph showing datapoints and curves fitted thereto for an assay according to the invention with ritonavir. The X-axis denotes the fraction of human plasma in the total solution (in ml/ml), while the Y-axis denotes the counts for each specific volume of polymer coating (in nl, given for each curve) in each well. As expected, increasing the fraction of human plasma leads to lower partitioning to the polymer coating, and increasing the polymer coating leads to a higher partitioning to the coating. Experiments were conducted in 96 well plates, where the total volume was 200 µl.

DETAILED DESCRIPTION

The invention provides a simple and reliable assay for the determination of binding of hydrophobic drugs to other molecules or biological components, such as (plasma) proteins. The actual measurement is preferably performed in a simple, standard 96-wells microtiter plate, but should be feasible in any assay setting in which a plurality of vessels (at least two) is available. Thus, a plate having at least two wells is the minimal requirement for performing the assay of the invention. However, a standard 96-wells assay is advantageous, since these are commercially available in large amounts and are relatively cheap, and since an assay with a plate having multiple rows and columns of wells allows for a statistically more reliable measurement or more measurements on one plate, and makes a generic approach possible for new chemical entities (NCEs) within a rather large range of hydrophobic and/or protein binding properties. Further, laboratory apparatuses like optical readers are suited for and also work with standard 96-wells plates.

The assay of the present invention in which the coefficient of binding of a hydrophobic compound to another compound, such as a macromolecule like a protein or a DNA sequence, or to a biological component, such as a cell or receptor complex is measured, introduces a third variable: a polymeric coating of the well. Because of this polymer the hydrophobic compound is extracted from the assay solution by a process indicated as partition extraction.

Partition extraction is a process in which, generally with the aid of an extracting polymer, amounts of ligand present in solution (in the present invention, the hydrophobic compound) are removed from the solution by extraction in or to an extracting (usually solid) phase, as a result of which an equilibrium shift might occur between free ligand and bound ligand in a solution. In general, a solid phase is used for the extraction, but a polymeric or any other immiscible liquid or liquid crystalline may be used as well. Such embodiments of "solid phases", which are part of the present invention, in any case have the capability to remove free ligand from the solution by absorption or adsorption. Where the term "solid phase" is used in the present specification, this is only used to indicate a specific working principle. The present invention is not limited to extracting solid phases which can remove ligands from a liquid. Therefore, in a general sense, this is referred to as an extracting phase herein. This extracting phase is characterized in that the bound ligand is absorbed therein and is thereby removed from the liquid as a free ligand. A characteristic of the partition extraction which is part of the aspects of the present invention is that essentially only a part of the total amount ligand is extracted, and thus an equilibrium will be established between the amount of free ligand. and extracted ligand.

Herein, a "free" ligand has the meaning of a ligand freely present in solution, both in contrast with a ligand bound to the binding partner and in contrast with a ligand extracted by the extracting phase. So, herein, a free ligand is unbound and not extracted. In the specific embodiment of the present invention, the ligand is the hydrophobic compound and the binding partner is the (plasma) protein or biological component.

Solid phase microextraction (SPME) is an extraction technique which makes use of a polymer-coated fiber as the extraction tool (Arthur and Pawliszyn, 1990, Anal Chem 62, 2145-2148). After the extraction, the relevant compound can be desorbed from the fiber and then be analyzed by means of techniques appropriate to that end such as for instance GC or HPLC. One of the properties of SPME is that only the freely dissolved fraction of the compound is available for partitioning to the extraction tool. Another property of SPME is that the method can be used in such a manner that only small amounts are extracted from the sample. The present invention provides the solid phase as e.g. a coating of the sample container, so that the determination can be carried out more simply.

If a known amount of a known ligand and a macromolecule or biological component are brought together in solution, then the amount of ligand which is still freely present in solution will depend on the concentration and the coefficient of binding to the macromolecule or biological component. Binding to macromolecules or biological components is generally an equilibrium process.

In a solution in which, as an example of a macromolecule or biological component, a binding protein and a hydrophobic compound are present, in which further an extracting phase as described hereinabove is present, the concentration of the compound in the extracting phase is a good reflection of the concentration of the compound freely present in solution, and is thus not bound to the binding partner. In this respect both the absolute amount of the extracting phase as well as the total volume of solution are of influence on the capacity of the compound that can be extracted. However, by keeping the volume of the solution constant and by varying the concentration of the polymer over a row (or column) of wells on the assay plate, it is possible to create a series of test cells in which the equilibrium shifts. Alternatively, the concentration of the polymer can be kept constant and the volume of the test solution is varied. The concentration of the free compound present in the extracting phase can be determined with various methods, which methods will be described in more detail hereinbelow.

Methods according to the invention can be used to determine the binding coefficient of a wide range of hydrophobic substances with a specific binding macromolecule or biological component. The reason why the bound compound is substantially not extracted by the extracting phase is the result of the increased molecular weight of the formed complex compared to the free forms of compound. Only the low molecular compound freely present in solution can be extracted in order to be able to detect and/or measure (the amount of) the compound freely present in solution in that manner.

Preferably, low-molecular hydrophobic compounds such as steroids and benzodiazepines (such as valium), different hydrophobic antibiotics and substances such as vitamins, particularly vitamin D, are measured. Other examples of suitable compounds are quercetin, estradiol, estriol, cannabinoids, ACE-inhibitors (angiotensin II antagonists) and new chemical entities as developed in the pipelines of the pharmaceutical industry. Herein, low-molecular is understood to mean a molecular weight of 100-2000 Da, preferably in a range from about 150 to about 1000 Da.

The compound to be detected preferably is not labelled, such as a radioactively labeled form. Any type of labelling that does not influence the physicochemical properties of the compound would be applicable. Methods how to measure concentration of labeled compounds are well known to the person skilled in the art. It is also possible that a compound is not labeled, it can then be detected by known methods such as HPLC, GC, LC-Ms, etc.

Very suitable binding partners are binding partners which result in a complex with the compound which cannot be extracted by the extracting phase due to their molecular weight or due to their size, while free hydrophobic compound can be extracted by the extracting phase. In general, macromolecular structures with a Mw>1000-2000 Da are too large to be extracted by the extracting phase. Therefore, preferably binding partners are used which cause the molecular weight of the ligand to increase to a value higher than 1000 Da, more preferably higher than 2000 Da. With great preference, plasma or plasma proteins, antibodies, receptors, BSA, phospholipid vesicles, and the like are used as binding partners.

Other suitable binding partners are, for instance, cell systems, e.g. cells or tissues or homogenates thereof, which contain a particular binding macromolecule or homogenates of tissue or cells which contains a particular binding macromolecule, etc. A preferred binding partner are plasma proteins. These plasma proteins can be serum albumine, but also less abundant protein species such as immunoglobulins, clotting factors, and the like, or combinations of these. In a preferred embodiment, the binding partners are all the available proteins in a sample, where such a sample consists of plasma from a human or animal source.

The binding partner is provided in an increasing concentration in each column of the assay plate. Preferably, the binding partner is provided in a concentration in the range from about 1 attomol/L to about 10 mol/L, preferably from 1 nanomol/L to about 10 mmol/L, more preferably in the range from about 1 picomol/L to about 100 micromol/L, and still more preferably from about 10 picomol/L to about 10 micromol/L. The advantage of a method according to the present invention is that the binding partner can be applied in very small amounts. The detectable compound to be investigated can, if present, be provided in any suitable concentration and this concentration preferably is the same in each well of the assay. The ligand to be investigated can be provided in a concentration in the range from about 1 attomol/L to about 1 mol/L, preferably from about 1 picomol/L to about 1 millimol/L.

Thus, while the concentration of the extracting phase is varied from row to row, and the concentration of the binding protein is varied from column to column, the concentration of the low molecular hydrophobic compound is kept the same.

In this way n measurements (wherein n is the number of columns times the number of rows), preferably 96, and minimally 2 measurements can be taken. In each measurement the concentration of the hydrophobic compound in the extracting phase, or in the liquid phase, or both is determined. The concentration in the polymer is, at a constant pH, temperature and pressure, dependent on four parameters: the concentration of the binding partner, the total concentration of the ligand, the partition coefficient between polymer and aqueous phase and the binding coefficient between hydrophobic compound and binding partner. From these 4 parameters, two, the partition coefficients are unknowns, and these can be can be solved with at least 2 measurements, but, of course, a more reliable result is obtained in a multiplicity of test wells, especially a matrix of 8×12 wells, giving a total of 96 measurements, and especially a test well array in which the concentration of binding partner and/or the concentration of the extracting phase is provided in a series of amounts.

As a solvent for providing a solution of a binding partner, in principle many types of solvents can be used. It is important that the solvent makes the binding between binding partner and the hydrophobic compound possible. Preferably, water is used as a solvent. Many types of buffers are excellently suitable as an aqueous solvent. A skilled person is able to realize a suitable reaction environment, in which binding occurs between the binding partner and the hydrophobic compound. With great preference, human plasma or aqueous solutions in the form of a phosphate-buffered saline (PBS) are used as a reaction mixture for such a binding reaction. Equally applicable are TRIS/BSA buffers in which BSA is used as binding partner. A skilled person will understand that the choice of the solvent or medium depends on the compound to be detected and the binding protein.

In by far most cases, a method for measuring the binding of a hydrophobic compound will be carried out in a liquid. A method according to the present invention is in principle not limited to the detection and/or the measurement of compounds in a liquid. In principle, any sample is suitable to be subjected to a method according to the invention. If the sample is a solid or semi-solid sample, such as a tissue, the ligands to be investigated therein can be subjected to a method according to the invention by including the compounds in a liquid, preferably an aqueous liquid, preferably a medium in which binding between a binding partner and a hydrophobic compound and also extraction of free compound by the extracting phase can take place.

A method for measuring the binding of a hydrophobic compound according to the present invention comprises the step of subjecting the liquid to conditions in which the compound can bind to the binding partner in order to provide an amount of bound compound and an amount of free compound in the liquid. Here, the liquid is of course understood to mean the liquid containing the compound, which liquid may have the form of a reaction mixture. Here, subjecting the reaction liquid to conditions in which the compound can bind is understood to mean that the condition for binding of the compound to the binding partner not only needs to be facilitated, but also needs to be maintained for some time in order to enable binding of compound to the binding partner and consequently an equilibrium between bound and free compound. So, here, the pH, the temperature or a different condition parameter is important, as well as the time during which the reaction components are exposed to the conditions for binding. In this connection, suitable periods are periods varying from a few seconds to a few hours. Preferably, such a binding reaction is carried out for a period of about 1 minute to about 24 hours. Here, it needs to be borne in mind that the formation of free compound and bound compound is an equilibrium reaction in which the period in which the equilibrium is established can vary per ligand and per binding partner. A skilled person will be familiar with the possibilities for optimization of both the reaction environment and the reaction condition on the basis of the description hereinbelow.

A method for measuring the binding of a hydrophobic compound according to the present invention further comprises the step of subjecting the solution to a partition extraction in which a part of the amount of free compound is extracted to the extracting phase. To this end, the liquid, i.e. the reaction mixture with the free and bound hydrophobic compounds therein, needs to be contacted with an extracting phase. It is of course also possible that the liquid is already in contact with the extracting phase and that afterwards another reaction component, such as a binding partner, is added. Such an extracting phase may comprise an extracting surface. Thus, the surface of the inside of a reaction vessel may comprise an extracting phase in which extraction can take place. Such extracting phases can very suitably be applied in the form of a coating or cover layer to a surface which can be contacted with the reaction mixture so that that surface is provided with extracting properties. Suitable coatings or cover layers preferably comprise lipophilic polymers such as for instance polysiloxanes. Other polymers, such as polyacrylates, divinylbenzene, carboxylated PVC, cellulose acetate, "molecular imprinted polymers" (MIPs), and mixtures of polymers may also be used as an extracting phase. Preferably, polymers such as polydimethylsiloxane (PDMS) are used, more preferably with a Log Kd for the hydrophobic compound of between 1 and 8, preferably between 2 and 6. Such a binding layer may also be suitably applied to solid-phase particles present in the sample solution, e.g. beads from glass or plastic.

In the following paragraph, the working principle of the extraction is set forth with. By the (solid-phase) extraction, a fraction of the unbound compound freely present in solution (L<sol>) is removed from the solution in that a fraction of the unbound compound freely present in solution is extracted in an extracting phase. According to the methodology to be followed, however, a only part of the compound freely present in solution is extracted by the extracting phase. In a method according to the present invention, the reaction mixture is therefore subjected to partition extraction in which an extracting phase is used which can only bind a part of the compound freely present in solution. So, it is important that the capacity (that is, inter alia the combination of affinity and amount) of the extracting phase used to bind compound freely present in solution is limited and is chosen such that a partial extraction takes place. In order to limit this capacity (that is, inter alia the extraction efficiency), the amount of the extracting phase can be limited, for instance by limiting the dimensions of the thickness of an extracting coating layer or the surface an extracting coating layer or by, for instance, limiting the amount of an extracting coating layer applied to an inner wall of a reaction vessel. In a preferred embodiment, in a method according to the invention, a reaction mixture is contacted with an extracting phase which is located on the inside of a reaction vessel (liquid container) and which comprises an extracting polysiloxane in the form of a cover layer of which the amount is limited so that only a part of the compound can be extracted thereby. The extraction of the free compounds ($L_{sol}$) by the extracting phase can substantially take place by absorption, but adsorption, adhesion or binding is suitable as well. The amount of extracting phase used to extract a predetermined fraction (for instance about 5%) or particular amount of the free compound ($L_{sol}$) thereof by means of the extracting phase depends on the partition coefficient (Kd) of the extracting phase used. With a partition coefficient of 10, the ratio of the amount (concentration) of compound extracted by the extracting phase ($L_{polymer}$) to the amount (concentration) of compound freely present in solution ($L_{sol}$) will be 10:1. On the basis thereof, a skilled person will be able to determine an amount (concentration) of extracting phase to be used. Because the extracting phase is primarily used to extract free compound ($L_{sol}$) from the liquid, the extracting phase is substantially such that no bound (conjugated) compound ($L_{conj}$) is bound thereto and preferably no free binding protein either. This can be provided by providing an extracting phase into which the bound compounds (the conjugates) ($L_{conj}$) and preferably also free binding partners cannot penetrate due to their size, but into which free compound ($L_{sol}$) can penetrate, for instance by means of diffusion, and can then absorb.

Further, a method for detecting and/or measuring a ligand according to the present invention comprises the step of detecting and/or measuring the extracted compound. The determination thereof may, for instance, be done by separating the liquid in which free compound is present from the extracting phase and determining the amount of compound in the extracting phase. The determination may be done by use of, for instance, chromatographic, (mass) spectrometric, and radiochemical detection techniques. The determination of the concentration of the hydrophobic compound may also take place in the solution. Preferably the total concentration of hydrophobic compound in the solution, i.e. the total of free and bound ligand should be measured.

It holds true for the compound that $L = L_{sol} + L_{conj} + L_{polymer}$, in which L is the compound, $L_{sol}$ is the fraction of free compound in solution, $L_{conj}$ is the fraction of bound compound and $L_{polymer}$ is the fraction of ligand in the extracting phase.

A skilled person will understand that there are a number of possibilities to determine $L_{conj}$ and from this the binding coefficient of L. A first step is the measurement of the amount of $L_{polymer}$ or the total of $L_{sol} + L_{conj}$, which is L minus $L_{polymer}$. This detection may take place by use of, for instance, chromatographic, (mass) spectrometric, and radiochemical detection techniques. As indicated, detection of the fraction of the compound extracted by the extracting phase may also be done by separating the reaction mixture or the solution from the extracting phase and detecting the compound without removing it from the solid phase. To this end, for instance a scintillation proximity assay (SPA) can be used as inter alia described in WO 02/101084. The scintillation proximity assay is based on the fact that 6 rays are emitted by compounds labelled with weak radioisotopes (such as $^3H$, $^{125}I$, $^{33}P$ and $^{35}S$), which can only cover a limited distance in an aqueous environment before their energy is lost completely. However, these emissions can be detected with high sensitivity if the compounds labelled with radioisotopes are brought in the immediate proximity of an extracting phase provided with a scintillator (such as for instance 2,5-diphenyloxazole) so that a specific emission is obtained. Radioactively labelled compounds which are freely present in solution are not detected because they are too far removed from the scintillating extracting phase. SPA technology is inter alia commercially available under the name FlashPlate® from NEN Life Science Products.

As indicated above, the amount of compound in the extracting phase is, next to the binding coefficient, also dependent on the concentration of binding partner and the partition coefficient between polymer and aqueous solution. Even if the concentration of binding partner is not exactly known (e.g. because there is a mixture of proteins comprised of binding and non-binding proteins, such as in plasma) the—overall—binding coefficient can be calculated since there are at least 2 measurements with the two unknown parameters. Further, in a preferred embodiment there will be at least 96 measurements, which enables a more reliable calculation of the amounts of $L_{sol}$ and $L_{conj}$. In the case that with two measurements, two parameters need to be determined (or in the case that one of the parameters, for example the polymer-water partition coefficient was determined beforehand) and thus, the degrees of freedom=0, this means that equations can be analytically solved. In the case that the degrees of freedom is greater than 0 (dF>0), a least-squares regression might be used to obtain the best estimate of these parameters.

Lastly, in another preferred embodiment, some of the test vessels will not contain binding partner, which results in an even simpler equation, which in addition to the other equations would facilitate solving the binding coefficient calculation.

EXAMPLES

Example 1

Materials and Methods 96-wells deepwell plates (lot 1450-401 Perkin-Elmer Lifesciences) were coated with dimethylsiloxane by making the solutions A-H here below in n-hexane. The used dimethylsiloxane (Silicone rubber, GE Silicones, Bergen op Zoom, The Netherlands) has a density of 1.06. Solution H contains 9.54 g dimethylsiloxane in 300 ml n-hexane.

| | | | | | | | |
|---|---|---|---|---|---|---|---|
| solution-A | | | | n-hexane | = | 0 nl/100 μl |
| solution-B | 100 ml solution-C | + | 200 ml | n-hexane | = | 4.11 nl/100 μl |
| soluton-C | 100 ml solution-D | + | 200 ml | n-hexane | = | 12.3 nl/100 μl |
| solution-D | 100 ml solution-E | + | 200 ml | n-hexane | = | 37 nl/100 μl |
| solution-E | 100 ml solution-F | + | 200 ml | n-hexane | = | 111 nl/100 μl |
| solution-F | 100 ml solution-G | + | 200 ml | n-hexane | = | 333 nl/100 μl |
| solution-G | 100 ml solution-H | + | 200 ml | n-hexane | = | 1000 nl/100 μl |
| solution-H | 9.00 ml = 9.54 g polysiloxane in 300 ml n-hexane | | | | = | 3000 nl/100 μl |

From solutions A-H 100 μl is pipetted in row A-H of each plate. Plates were dried to air for minimally 18 hours (overnight).

Plasma is diluted with saline according to the following scheme and the compounds to be tested (25-hydroxy vitamin D (25-OHD) and ritonavir) are added:

Plasma dilutions ml/ml, total volume 20 ml for 12 plates

| | 25-OHD and Ritonavir | | | Warfarin | | |
|---|---|---|---|---|---|---|
| | plasma μl | 0.9% NaCl μl | ml/ml | plasma μl | 0.9% NaCl μl | ml/ml |
| solution-1 | 0 | 20000 | = 0 | 0 | 20000 | = 0 |
| solution-2 | 10 | 19990 | = 0.0005 | 10 | 19990 | = 0.0005 |
| solution-3 | 16 | 19984 | = 0.0008 | 20 | 19980 | = 0.001 |
| solution-4 | 20 | 19980 | = 0.001 | 40 | 19960 | = 0.002 |
| solution-5 | 60 | 19940 | = 0.003 | 80 | 19920 | = 0.004 |
| solution-6 | 100 | 19900 | = 0.005 | 140 | 19860 | = 0.007 |
| solution-7 | 160 | 19840 | = 0.008 | 200 | 19800 | = 0.01 |
| solution-8 | 200 | 19800 | = 0.01 | 400 | 19600 | = 0.02 |
| solution-9 | 400 | 19600 | = 0.02 | 800 | 19200 | = 0.04 |
| solution-10 | 600 | 19400 | = 0.03 | 1600 | 18400 | = 0.08 |
| solution-11 | 800 | 19200 | = 0.04 | 3000 | 17000 | = 0.15 |
| solution-12 | 1000 | 19000 | = 0.05 | 4000 | 16000 | = 0.2 |

To each dilution of plasma (solutions 1-12) an identical amount of the compound to be tested is added (about 20,000 ppm/200 μl solution). As control a similar amount is put in a separate vessel. The solutions are incubated with the compound overnight at 4°.

Experimental Procedures

The plasma solutions 1-12 are added to corresponding columns 1-12 of each plate (200 μl/well). Also 200 μl was added to a separate vessel to be able to correct for (plasma concentration dependent) solubilization. The next day the plates are emptied, washed once with aqua bidest and dried. When sufficient dry in all wells 200 μl counting solution (Optiphase Hisafe 2, Perkin Elmer Lifesciences) is added and the plates are covered. After incubation for minimally 4 hours under gently shaking the radioactivity in each plate is determined using liquid scintillation counting with a MicroBeta device (Perkin Elmer).

Data Analysis

As an example for ritonavir the following counts were measured in the polymer coating on one plate:

| | plasma ml/ml | | | | | | | | | | | | coating (nl) |
|---|---|---|---|---|---|---|---|---|---|---|---|---|---|
| | 0 / 1 | 0.0005 / 2 | 0.0008 / 3 | 0.001 / 4 | 0.003 / 5 | 0.005 / 6 | 0.008 / 7 | 0.01 / 8 | 0.02 / 9 | 0.03 / 10 | 0.04 / 11 | 0.05 / 12 | |
| A | 2561 | 408 | 355 | 368 | 250 | 266 | 262 | 260 | 208 | 195 | 156 | 124 | 0 |
| B | 3274 | 3323 | 3033 | 2677 | 2391 | 2725 | 2605 | 2644 | 2135 | 1925 | 1501 | 1143 | 4.1 |
| C | 4727 | 5936 | 6243 | 6668 | 6779 | 7054 | 5943 | 6466 | 5288 | 4066 | 3633 | 2760 | 10.2 |
| D | 6222 | 9146 | 9649 | 10037 | 9818 | 10234 | 9899 | 9247 | 8673 | 6969 | 5932 | 5080 | 25.6 |
| E | 6561 | 14297 | 15214 | 15293 | 15161 | 15908 | 15892 | 15112 | 14665 | 13475 | 12160 | 10938 | 64 |

-continued

| | plasma ml/ml | | | | | | | | | | | | |
|---|---|---|---|---|---|---|---|---|---|---|---|---|---|
| | 0 | 0.0005 | 0.0008 | 0.001 | 0.003 | 0.005 | 0.008 | 0.01 | 0.02 | 0.03 | 0.04 | 0.05 | coating |
| | 1 | 2 | 3 | 4 | 5 | 6 | 7 | 8 | 9 | 10 | 11 | 12 | (nl) |
| F | 8997 | 16590 | 17344 | 17749 | 18112 | 18628 | 18582 | 18647 | 18017 | 17384 | 16322 | 16100 | 160 |
| G | 9656 | 17305 | 18129 | 18063 | 19067 | 19174 | 19405 | 19137 | 19188 | 18707 | 18174 | 17730 | 400 |
| H | 10194 | 17396 | 18254 | 18984 | 19314 | 19676 | 19541 | 19454 | 19218 | 19112 | 18716 | 18325 | 1000 |

As an example for 25-OH vitamin D the following counts were measured in the polymer coating of one plate:

| | plasma ml/ml | | | | | | | | | | | | |
|---|---|---|---|---|---|---|---|---|---|---|---|---|---|
| | 0 | 0.0005 | 0.0008 | 0.001 | 0.003 | 0.005 | 0.008 | 0.01 | 0.02 | 0.03 | 0.04 | 0.05 | coating |
| | 1 | 2 | 3 | 4 | 5 | 6 | 7 | 8 | 9 | 10 | 11 | 12 | (nl) |
| A | 1529 | 639 | 495 | 419 | 151 | 109 | 95 | 90 | 82 | 62 | 55 | 47 | 0 |
| B | 2095 | 1753 | 1176 | 972 | 399 | 257 | 212 | 169 | 98 | 75 | 68 | 48 | 4.1 |
| C | 3498 | 2581 | 1649 | 1545 | 603 | 428 | 372 | 293 | 182 | 130 | 87 | 70 | 10.2 |
| D | 4260 | 4428 | 3019 | 2658 | 1258 | 866 | 686 | 523 | 278 | 237 | 153 | 153 | 25.6 |
| E | 5814 | 8145 | 6029 | 5501 | 2547 | 1719 | 1054 | 641 | 409 | 342 | 296 | 64 | |
| F | 7292 | 12361 | 10164 | 9700 | 5687 | 3804 | 3035 | 2408 | 1394 | 988 | 722 | 588 | 160 |
| G | 8015 | 15727 | 13748 | 13183 | 9284 | 7410 | 5863 | 5093 | 3130 | 2209 | 1681 | 1354 | 400 |
| H | 8491 | 16960 | 15479 | 15022 | 11307 | 10375 | 9044 | 8309 | 5582 | 4228 | 3295 | 2501 | 1000 |

Additionally a total count was determined for each well. The total count is the count in the polymer coating+the count in the remaining fluid. The latter was determined by isolating 25 µl from solution in each well prior to emptying, and mixing with Optiphase (Perkin Elmer) followed by liquid scintillation counting.

Data Analysis Consisted of the Following:
1. For each datapoint for which the total count was determined, the recovery of total radioactivity was determined by comparing with the counts of the reference spiking solution. Cells with a total recovery <75% were excluded from further data analysis.
2. From all rows containing polymer, the a-specific binding, i.e. the corresponding counts from the row without polymer, was substracted.
3. Curve fitting was applied using the following formula for each cell:
Predicted counts in coating=$T_c/((1/ff_p+1/fp-1)\times(fp\times V_w)/K_{pdms}/V_p))$, where
$T_c$ is the corresponding determined total count for the specific well,
fp is the fraction of plasma in the aqueous phase for the specific well
$V_w$ is the total volume of the aqueous phase for the specific well,
$V_p$ is the volume of the polymer phase for the specific well,
$ff_p$ is the fitted free fraction for 100% plasma
$K_{pdms}$ is the fitted partition coefficient between the polymer and water.
The above formula was fitted using $ff_p$ and $K_{pdms}$ target parameters to be optimized using the least squares regression method over all wells that were included in the data analysis, by calculating the squared difference between the measured counts in the coating and the predicted counts in the coating.
Results
Free fraction for each compound was determined on six different 96 well plates and the total average results (given as ratio between free fraction and total concentration) were as follows:

| Compound | Free fraction ± s.d. |
|---|---|
| Ritonavir | 0.0230 ± 0.0034 |
| 25-hydroxy vitamin $D_3$ | 0.000502 ± 0.000060 |

This example shows that a very reliable measurement of the plasma binding of hydrophobic compounds can be obtained in a simple and fast way.

The invention claimed is:
1. Method for the determination of the binding coefficient of a hydrophobic chemical compound comprising:
  a. Providing an assay plate with a plurality of wells including rows and columns of test vessels;
  b. Providing the test vessels in said assay plate with a polymer, wherein in each row the amount of polymer coating per test vessel is increased, and wherein said polymer is capable of extracting an extracted fraction of said hydrophobic chemical compound;
  c. Filling each test vessel with a solution of binding partner to which the binding coefficient should be assayed, wherein in each column the amount of binding partner is increased and wherein said binding partner is capable of binding a bound fraction of said hydrophobic chemical compound;
  d. Adding the hydrophobic compound and incubate the plate;
  e. Determining the concentration of said compound in said polymer or in the solution;
  f. Calculating the binding coefficient of the compound.
2. Method according to claim 1, wherein the assay plate is a 96-wells microtiter plate.
3. Method according to claim 1, wherein the polymer is a thin film polymer.
4. Method according to claim 3, wherein the polymer is coated in each well.
5. Method according to claim 3, wherein the polymer is a lipophilic polymer.

6. Method according to claim 1, wherein said binding partner is a protein.

7. Method according to claim 1, wherein said binding partner is a cellular component.

8. Method according to claim 7, wherein the protein solution is an aqueous solution.

9. Method according to claim 5, wherein the lipophilic polymer is selected from the group consisting of polysiloxanes polyacrylates, divinylbenzene, carboxylated PVC, cellulose acetate, "molecular imprinted polymers" (MIPs), and mixtures thereof.

10. Method according to claim 9, wherein the lipophilic polymer is poly(dimethylsiloxane).

11. Method according to claim 6, wherein the protein is a plasma protein.

12. Method according to claim 6, wherein the protein is selected from the group consisting of human serum albumin, immunoglobulins, and lipoproteins.

13. Method according to claim 7, wherein the binding partner is a lipid vesicle or a lipid membrane.

14. Method according to claim 8, wherein the protein solution is plasma.

\* \* \* \* \*